United States Patent
Grevious

[11] Patent Number: 5,562,714
[45] Date of Patent: Oct. 8, 1996

[54] MAGNETIC FIELD STRENGTH REGULATOR FOR IMPLANT

[75] Inventor: John J. Grevious, Minneapolis, Minn.

[73] Assignee: Medtronic, Inc., Minneapolis, Minn.

[21] Appl. No.: 383,040

[22] Filed: Feb. 3, 1995

[51] Int. Cl.$^6$ .................................................. A61N 1/362
[52] U.S. Cl. ................................................. 607/32; 607/60
[58] Field of Search .................................... 128/903, 902, 128/32; 455/41, 66, 116, 127

[56] References Cited

U.S. PATENT DOCUMENTS

| | | |
|---|---|---|
| 4,142,533 | 3/1979 | Brownlee . |
| 4,231,027 | 10/1980 | Mann et al. . |
| 4,324,251 | 4/1982 | Mann . |
| 4,332,256 | 6/1982 | Brownlee . |
| 4,541,431 | 9/1985 | Ibrahim . |
| 4,542,532 | 9/1985 | McQuilkin . |
| 4,556,061 | 12/1985 | Barreras . |
| 4,611,127 | 9/1986 | Ibrahim . |
| 5,117,825 | 6/1992 | Grevious . |
| 5,170,414 | 12/1992 | Silvian . |
| 5,324,315 | 6/1994 | Grevious . |

*Primary Examiner*—William E. Kamm
*Assistant Examiner*—Scott M. Getzow
*Attorney, Agent, or Firm*—Thomas F. Woods; Curtis D. Kinghorn; Harold R. Patton

[57] ABSTRACT

An efficient low cost means for regulating the output level of a magnetic field transmitter. A feedback coil tightly coupled to an output coil is designed to produce an output voltage just above the supply level for the output stage of the transmitter when the desired output level is achieved. The feedback sense coil tightly coupled to an output coil is designed to produce an output voltage just above a regulated power supply level for the output stage of the transmitting antenna until a desired output level is achieved. The feedback coil is diode coupled to the regulated power supply lines of the transmitter. When the output level increases above the regulation level the diodes begin to conduct returning energy to the supply and preventing further increase of the transmitting antenna signal.

13 Claims, 6 Drawing Sheets

MAGNETIC FIELD STRENGTH REGULATOR FOR IMPLANT

BACKGROUND OF THE INVENTION

1. Field of the Invention

The present invention generally relates to medical devices, and more particularly, to a technique for regulating the output level of a magnetic field transmitter for controlling implantable devices.

2. Description of the Prior Art

As implantable medical devices in general and cardiac pacers in particular became more complex in operation, the desirability for non-invasive transfer of data between the implant and an external device could be seen. In cardiac pacing, transfer of signals from an external device to the implant to modify operating parameters is called programming. Data is also transferred from the cardiac pacer to the external device to provide various monitoring information. These transfers are often termed telemetry.

U.S. Pat. Nos. 4,142,533 and 4,332,256 both issued to Brownlee et al., describe one approach to data communication between an implanted cardiac pacer and an external device. Though the primary feature discussed is telemetry of monitoring data from the implant, the importance of a non-invasive approach is emphasized.

A specifically two-way transmission system is shown in U.S. Pat. No. 4,231,027 issued to Mann et al. A similar system is shown in U.S. Pat. No. 4,324,251 issued to Mann. From these references, it can be seen that close proximity of receiver and transmitter is anticipated. In U.S. Pat. No. 4,556,061 issued to Barreras et al., the use of either magnetic coupling or radio frequency signals is discussed. In U.S Pat. No. 5,117,825 issued to Grevious, the use of a three frequency closed loop design which renders a second order system characteristic is discussed.

From all of these references, it is clear that the current state of art generally provides for transfer between an external programming device and an implanted medical device using a radio frequency carrier employing very close spacing of the transmitting and receiving antennas. Such close spacing provides low power operation for a given minimum signal to noise ratio in accordance with the well known inverse square law.

Unfortunately, this close spacing causes the metallic case of the cardiac pacer, along with the enclosed receiving antenna, to have a major impact upon transmitter antenna tuning and loading. In practice, this means that small changes in positioning of the external antenna (the position of the implanted antenna is assumed to be fixed) can cause large percentage changes in the inter-antenna spacing. The result is that transmitter antenna loading varies greatly from patient to patient and even within a single transmission for a particular patient if the transmitter antenna is moved even slightly. Antenna tuning is similarly affected by the relative change of position of the implanted pulse generator within the transmitter field.

SUMMARY OF THE INVENTION

The present invention overcomes the disadvantages found in the prior art by providing a first order transmitting system which controls the output magnetic field strength without envelope overshoot of the rise time during turn-on. Such control of the field strength of the transmission ensures constant field strength in view of normal variance in component values during the manufacturing process.

To accomplish the objects of the present invention, a separate feedback sense coil is placed in the same package as the transmitting antenna. In most cases this package is a puck-like transmission head which is electrically coupled to the external programmer electronic circuits. The feedback sense coil receives a signal which is proportional to the transmission field strength of the generated magnetic field. The relative positioning of the transmitting antenna and the feedback sense coil is fixed by the design of the transmission head.

Also placed in the transmission head with the feedback sense coil and transmitting antenna are a radio frequency amplifier, a tuned tank circuit, and a feedback element. The signal received by the feedback sense coil is diode coupled to the regulated power supply lines of the transmitter. When the magnetic field level increases above the regulation level the diodes begin to conduct returning energy to the positive and negative supplies and preventing further increase of the transmitting antenna signal, that is the transmitted magnetic field. Also as output loading occurs at the interface between the transmitting antenna and a cardiac pacer the degree of feedback is decreased and the output level is maintained within the drive capability the output stage. Hence, the feedback mechanism serves to regulate the operating Q of the transmitting antenna by direct loading of the magnetic field. Moreover, the direct loading of the H field not only yields a greater operating efficiency, but also conserves energy by returning the current conducted through the feedback diodes, which are coupled to the sense coil, to the regulated power supplies.

The circuit elements of the transmitter are combined to form a closed loop configuration which has a first order system characteristic, hence there is no risk of envelope overshoot at turn-on. Also the transmitter circuit is simple to operate given the characteristics of a first order closed loop design which only requires a precision tuned antenna to control the oscillating frequency and two diodes.

In contrast, the prior art system disclosed in the above-cited patent issued to Grevious requires a closed loop design which renders a second order system characteristic, and employs a feedback system based on direct measurement of the field strength, using a sampling technique. This closed loop design contains three interactive frequency elements, a tuned resistor-capacitor based oscillator, and a tuned inductor-capacitor radio frequency amplifier to drive an inductor based tuned antenna. The inclusion of three frequency elements in the design then requires precision control of the elements involved for frequency alignment, whereas the present invention only requires a precision tuned antenna to control the oscillating frequency.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numbers designate like parts throughout the figures thereof and wherein.

DETAILED DESCRIPTION OF THE PREFERRED EMBODIMENTS

Figure 1:
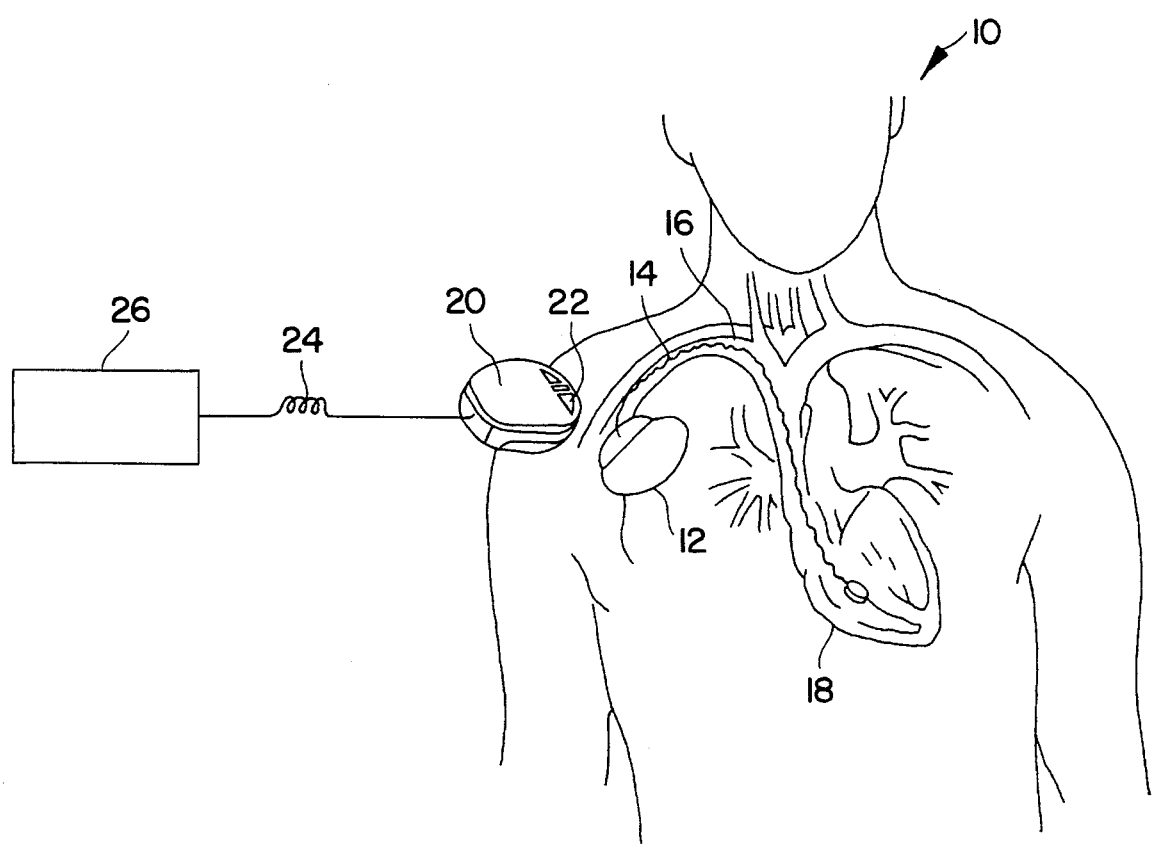
FIG. 1 is a diagram of a cardiac pacing system employing the present invention.

FIG. 1 illustrates a cardiac pacing system used to treat patient 10. The hermetically sealed implantable pulse generator 12 is implanted beneath the skin of patient 10 in the upper chest region. It is electrically coupled via insulated pacing lead 14 through the venous system 16 to heart 18.

The operating parameters of implantable pulse generator 12 are non-invasively programmed by the attending medical personnel using the electronic circuitry of external programmer 26. A control signal is sent from external programmer 26 via cord 24 to transmission head 20. This control signal causes the electronic circuitry within transmission head 20 to generate the radio frequency signal.

To program implantable pulse generator 12, the attending medical personnel enter the parameter data into external programmer 26. Transmission head 20 is placed on the skin of patient 10 in close proximity to implantable pulse generator 12. The button 22 shown positioned on transmission head is pressed to enable transmission of the programming data via the radio frequency carrier.

Figure 2:
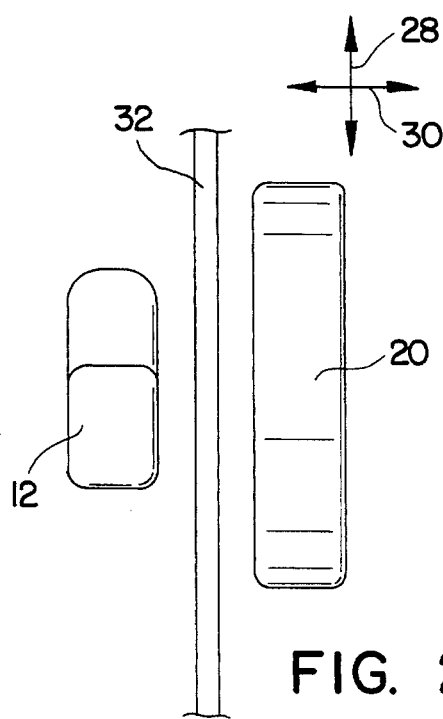
FIG. 2 is an end view of the relative positioning of the implanted device and transmission head.

FIG. 2 is a cutaway end view of the relative positions of implantable pulse generator 12 and transmission head 20. Ordinarily, the transmitting antenna within transmission head 20 and the receiving antenna within implantable pulse generator 12 will not be separated by much more than the thickness of skin layer 32 (FIG. 2 shows a slight separation for clarity).

Under normal conditions, implantable pulse generator 12 will be stationary with respect to skin layer 32 because the implant has been properly sutured into place and subsequent biological growth maintains this position chronically. Transmission head 20 similarly can not move significantly in the direction of arrow 30 if it is to rest on skin layer 32. However, transmission head 20 is free to move in the direction of arrow 28 and in the direction of a line (not shown) which is mutually perpendicular to arrows 28 and 30. This may be caused by the medical attendant as a result of misplacement of transmission head 20 or may even occur during a transmission by physical movement of transmission head 20.

It is apparent that the metallic enclosure of implantable pulse generator 12 is sufficiently close to transmission head 20 during transmission to significantly effect its tuning and load characteristics. Movement along arrow 28 or along the line mutually perpendicular to arrows 28 and 30 will, therefore, greatly impact transmission performance.

Figure 3:
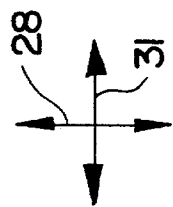
FIG. 3 is a top view of the relative positioning of the implanted device and transmission head.
Figure 3:
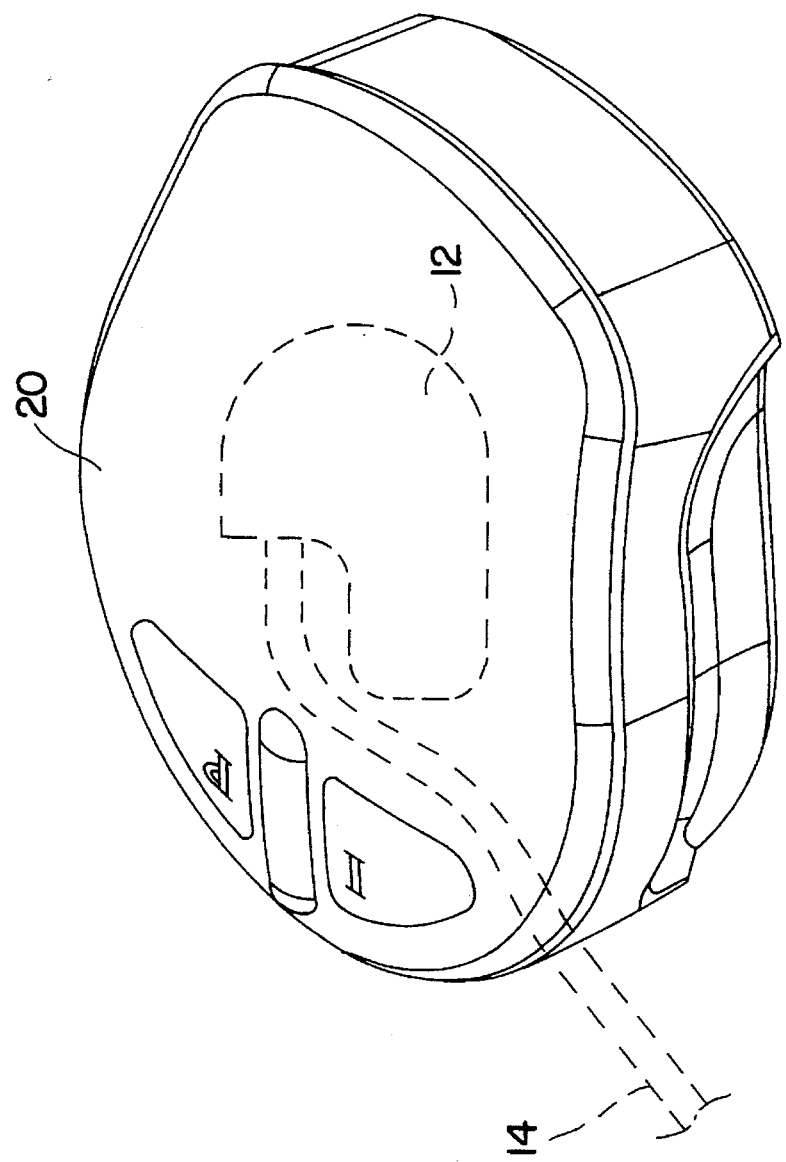

FIG. 3 is a top view of transmission head 20 positioned over implantable pulse generator 12 (shown in phantom). It can be seen in this view that the medical attendant is free to move transmission head 20 in the plane of arrows 28 and 31, where arrow 31 indicates movement along the skin surface and parallel to the implanted pulse generator 12. Movement in the direction of arrows 28 an 31 will impact the centering of implantable pulse generator 12 within the transmitting antenna (not shown) of transmission head 20. The loading of this transmitting antenna is thereby changed by the proximity of implantable pulse generator 12.

Figure 4:
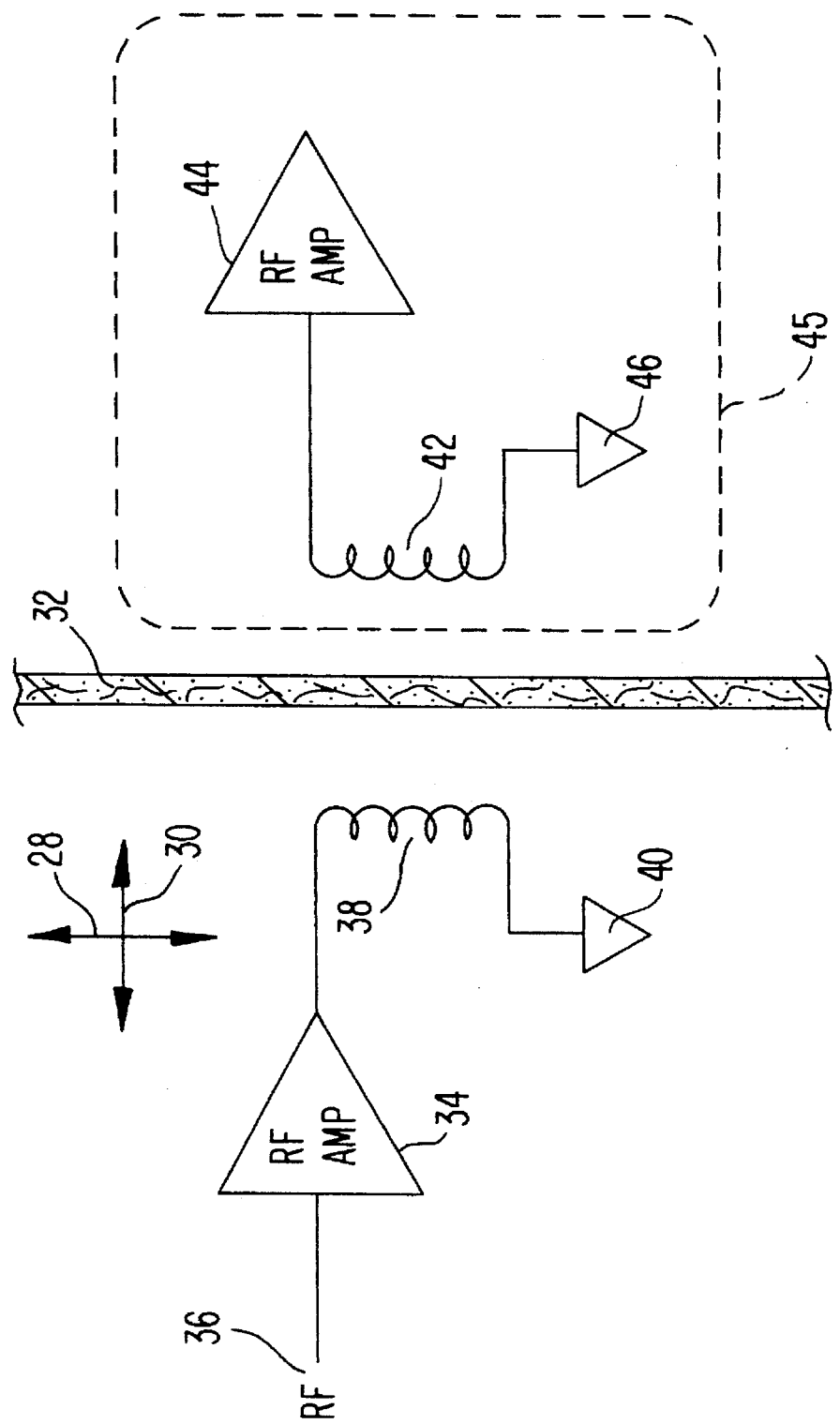
FIG. 4 is a schematic diagram of the major transmission components.

FIG. 4 is an electrical schematic of the key elements which serve to transfer data between the external programming device and the implantable pulse generator through skin layer 32. The modulated radio frequency signal 36 is supplied to radio frequency amplifier 34. The amplifier signal is conducted through transmitting antenna 38 to signal ground 40.

The electromagnetic field generated by transmitting antenna 38 induces a radio frequency signal in receiving antenna 42 between radio frequency amplifier 44 and signal ground 46. The output of radio frequency amplifier 44 is demodulated and processed in the manner known in the art.

In accordance with the previous discussion, the loading and tuning, and therefore, impedance of transmitting antenna 38 is effected by the close proximity of receiving device shield 45 and receiving antenna 42. This in part determines the current which flows in transmitting antenna 38, and thereby the strength of the resulting electromagnetic field. A change in the strength of this electromagnetic field changes the strength of the signal induced within receiving antenna 42, thus changing the signal level of the received signal.

Figure 5:
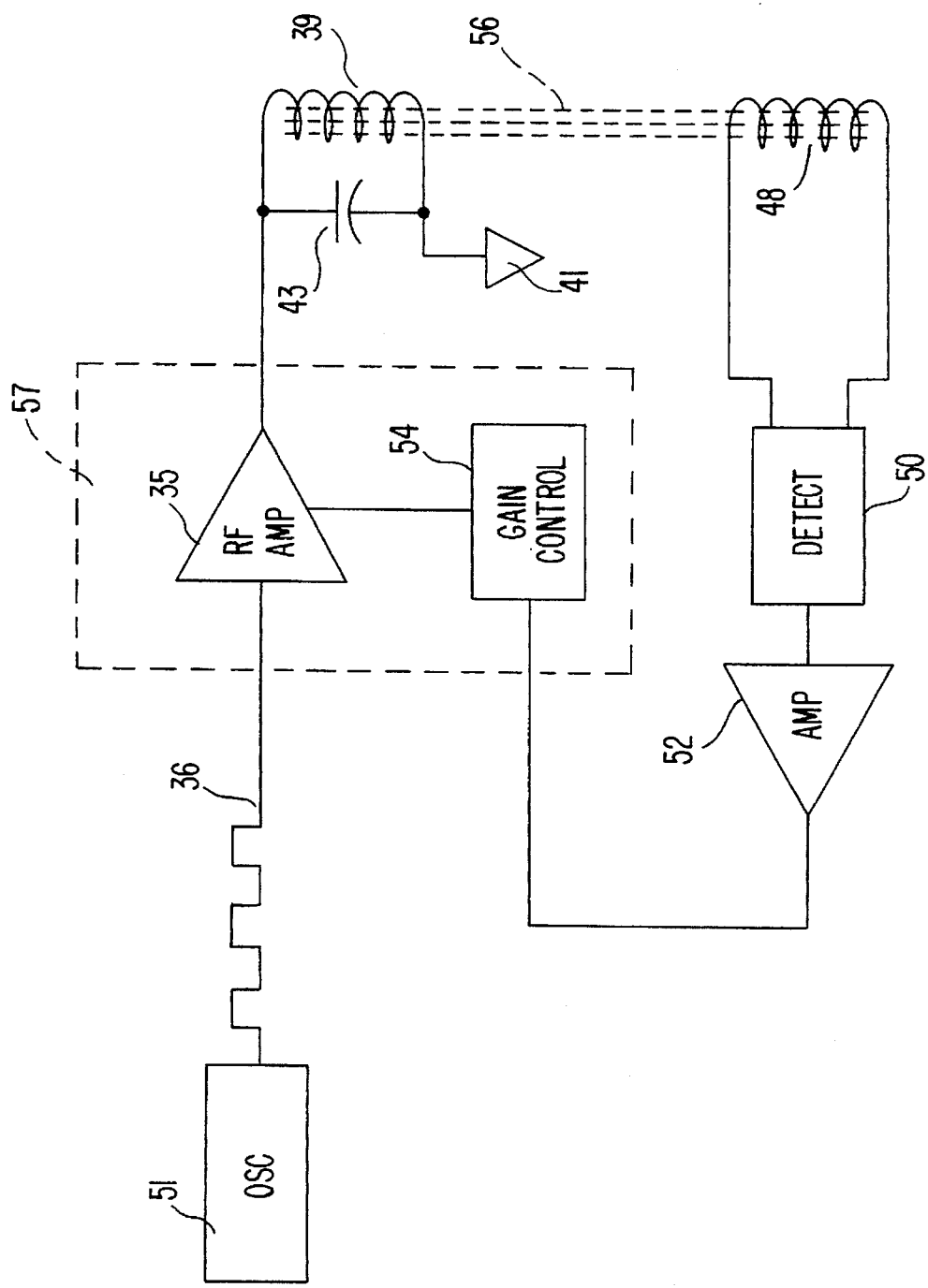
FIG. 5 is a schematic diagram of the feedback loop of the prior art.

FIG. 5 is a schematic diagram of elements of the prior art implementation of the cited Grevious patent. Modulated radio frequency signal 36 with a 50% duty cycle is generated from a class CE oscillator 51 and amplified by a variable gain radio frequency amplifier 35 operating in class "C" in conjunction with a tuned antenna. The amplified output current oscillates between transmitting antenna 39 and tuning capacitor 43. Core 56 is shared with sensing feedback antenna 48 to ensure close and fixed coupling of transmitting antenna 39 and sensing feedback antenna 48.

The signal induced in sensing feedback antenna 48 as a result of this coupling is proportional to the current flowing in transmitting antenna 39. This induced signal is detected by detector 50. The output of detector 50 is amplified by amplifier 52 and is used to control the variable gain of radio frequency amplifier 35 via gain control 54, which together function as a variable monostable one shot 57. The object of this control is to maintain a constant radio frequency current within transmitting antenna 39 during transmission. This constant current ensures a constant electromagnetic field held notwithstanding the loading impact caused by the close proximity of the receiving antenna.

Figure 6:
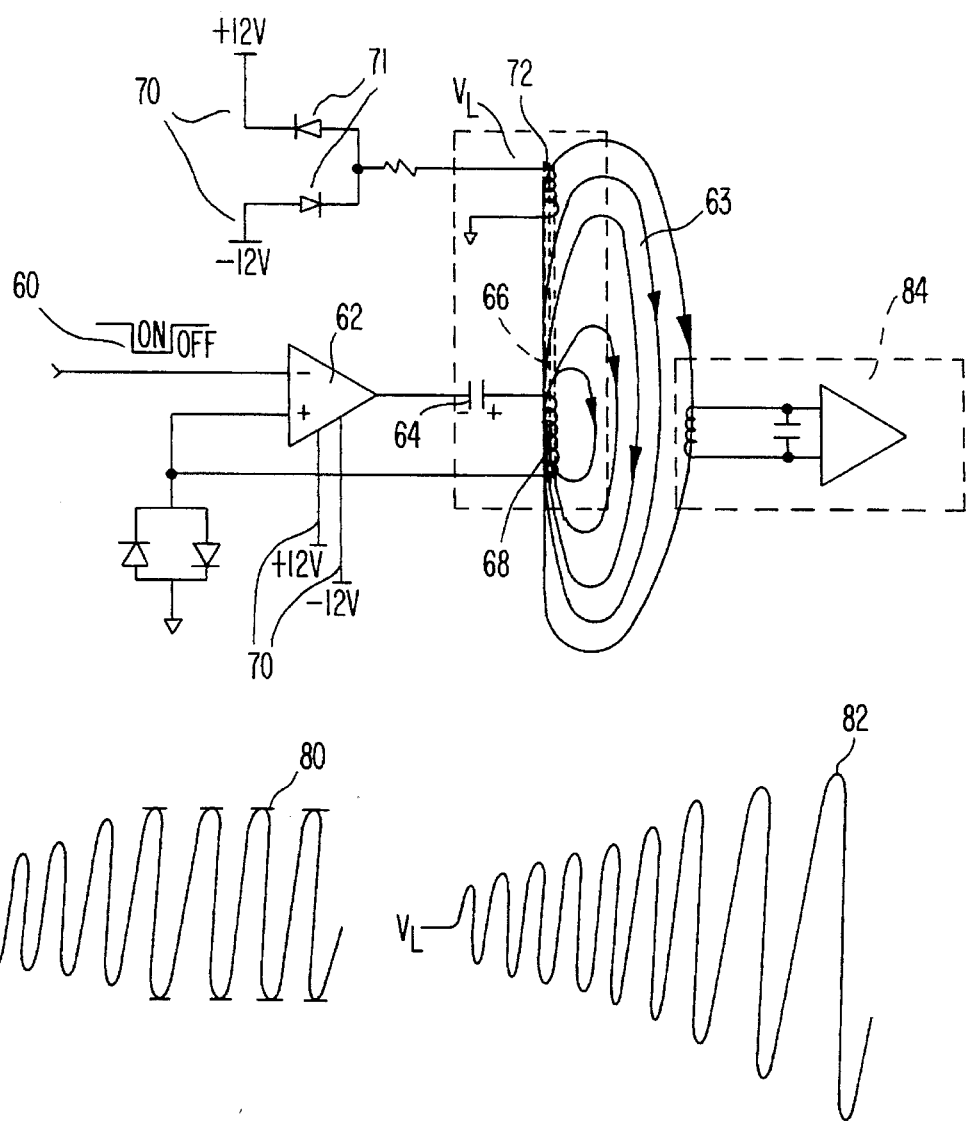
FIG. 6 is a schematic diagram of the feedback loop of the present invention.

Turning to FIG. 6 is a schematic diagram of elements of a telemetry system practicing the present invention. A modulated active low software controlled radio frequency signal 60 with a 50% duty cycle is generated from is from external programmer 26 in FIG. 1. This signal then activates a variable gain radio frequency amplifier 62 which is powered by a regulated supply 70. Further, amplifier 62 has a complementary metal oxide semiconductor, CMOS, output driver operating in conjunction with tuned antenna 68 and feedback capacitor 64 to define the resonant pole frequency desired. The output of amplifier 62 drives transmitting antenna 68 and tuning capacitor 64. An air core 66, as known in the art, is shared with sensing feedback antenna 72 to ensure close and fixed magnetic coupling of transmitting antenna 68 and sensing feedback antenna 72.

The voltage $V_L$ induced in sense coil 72 is proportional to the H field 63 as well as the voltage induced on transmitting antenna 68. When the voltage as seen by the sense coil 72 is less than the turn-on voltage of diodes 71 the diodes appear as a high impedance node. As the induced voltage $V_L$ as seen by the sense coil reaches the required diode voltage for turn-on a non-linear feedback current is conducted through the sense coil due to the non-linear characteristics of the diodes. At the point when the diodes 71 begin conducting is when the present invention begins to regulate the magnetic field 63. As the voltage $V_L$ induced by the magnetic field increases above the regulated supply level, (i.e. +/−12v), the diodes 71 will begin to conduct returning energy to the regulated supply, moreover, preventing further increase of the magnetic field. When loading of the H field occurs the degree of feedback is decreased and the output level of the H field is maintained. Hence, the feedback element 72 serves to regulate the operating Q of the transmitting antenna by direct loading of the H field, which regulates the Q of the transmitting antenna to render the required magnetic field output. In normal circumstances, the amplitude of the R-F signal applied to transmitting antenna 68 is sufficient to insure that diodes 71 will conduct, thus providing for a constant magnetic field.

During regulation the sense coil 72 is loaded and appears as a secondary winding due to the conducting diodes which reflects a lower impedance load to the primary coil or transmitting antenna 68. Also, conduction through the non-linear load generates a discontinuous output 80 as seen by $V_L$, that is, a clipped sinusoid versus a continuous sinusoidal output 82 prior to regulation. Moreover, during the regulation of the H-field the diodes 71 continue to conduct a non-linear current. Hence, as conduction occurs at the peaks of the discontinuous, non-linear, output 82 the transmitting antenna renders a lower Q during the transmit operation to the implantable cardiac pacemaker 84.

Figure 7:
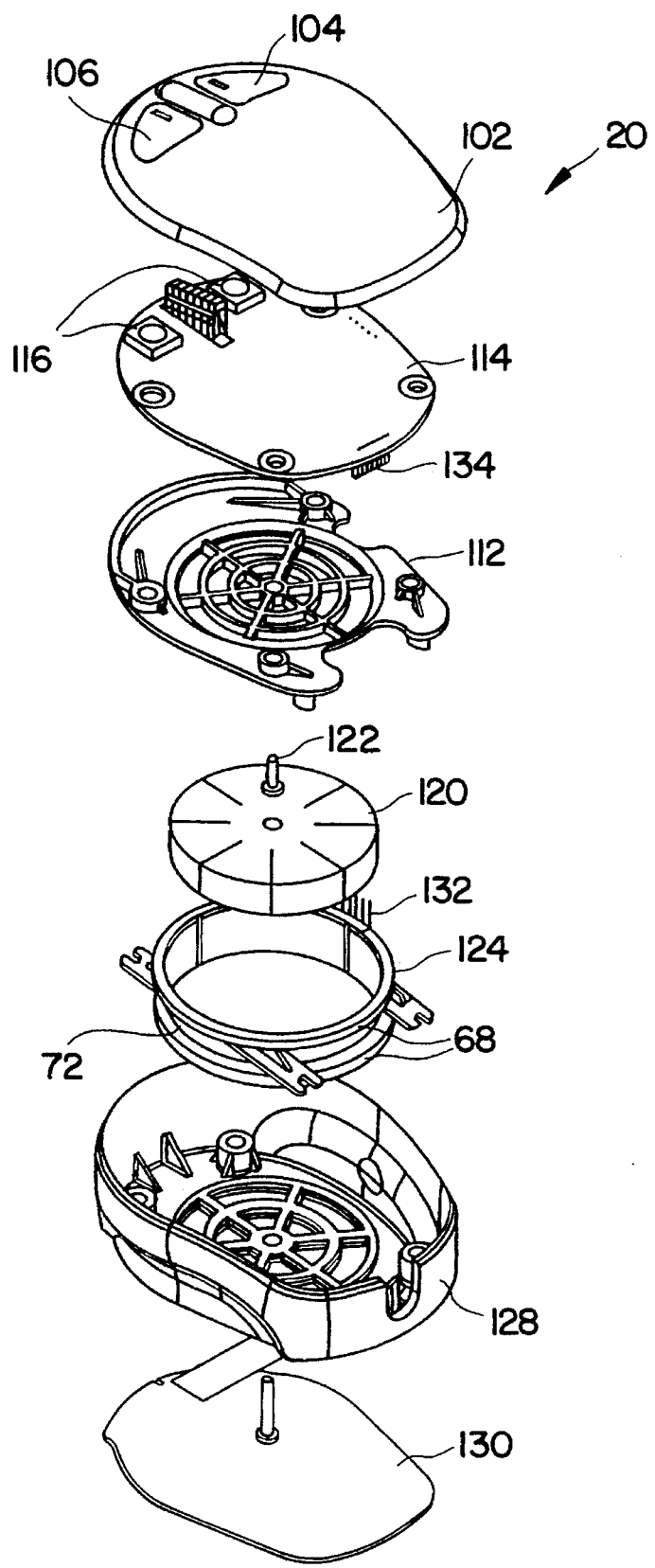
FIG. 7 is an exploded view of the transmission head of the present invention.

FIG. 7 is an exploded view of the transmission head 20. The transmission head comprises an upper case member 102 which attaches to lower case member 128. Upper case member 102 contains operator push buttons 104 and 106 which are coupled to printed circuit board 114 by switches 116. Printed circuit board 114 contains the electronic circuitry to generate and control the radio frequency signal. Retainer 112 aligns and connects printed circuit board 114 to upper case member 102. Also, retainer 112 provides shielding at the lower surface of printed circuit board 114.

Magnet 120 is used to activate the reed switch located in the implanted pulse generator as is known in the art. Pin 122 is employed to align magnet 120 to retainer 112. Antenna shield 123 provides a housing for magnet 120 which attaches to the lower case member 128. Label 130 is adhesively attached to the underside of transmission head 20 to provide a non-slip surface.

Antenna shield 124 contains the transmitting antenna 68 and feedback antenna 72 both of which are tightly coupled to produce an output voltage. Printed circuit board 114 and antenna shield 124 are electrically coupled via connector assembly 132 through the side of retainer 112, and connector assembly 134 electrically couples transmission head 20 to cord 24.

Having thus described the preferred embodiments of the present invention, those of skill in the art will be readily able to apply the teachings found herein to yet other embodiments within the scope of the claims hereto attached.

I claim:

1. A medical device system, comprising:

an implantable medical device having a receiving antenna;

an external programmer means for transmitting information to a pacemaker including a transmitter, said transmitter in turn comprising:

a transmitting antenna;

means for supplying a radio frequency signal to said transmitting antenna to cause generation of a magnetic field;

means for sensing strength of said magnetic field; and means responsive to said sensing means for variably loading said magnetic field to regulate said magnetic field strength, said loading means loads said magnetic field to restrict said field to a predetermined maximum level.

2. A system according to claim 1, wherein said loading means loads said magnetic field to maintain a constant magnetic field.

3. A system according to claim 1, wherein said loading means comprises means for regulating Q of said transmitting antenna.

4. A system according to claim 3 wherein said sensing means comprises a sensing antenna having an electrical connection through diodes to a power supply so that the Q of said transmitting antenna is regulated by draw down of energy by said sense antenna through said diode connection to said power supply.

5. A medical device system, comprising:

an implantable medical device having a receiving antenna;

an external programmer means for transmitting information to a pacemaker including a transmitter, said transmitter in turn comprising:

a transmitting antenna;

means for supplying a radio frequency signal to said transmitting antenna to cause generation of a magnetic field;

means for sensing strength of said magnetic field, said sensing means further comprises a sensing antenna; and means responsive to said sensing means for variably loading said magnetic field to regulate said magnetic field strength, said loading means further comprises means for allowing current flow through said sensing antenna in response to said magnetic field reaching a predetermined level.

6. A programmer for transmitting information to an implantable medical device by means of a transmitter, said transmitter in turn comprising:

a transmitting antenna;

means for supplying a radio frequency signal to said transmitting antenna to cause generation of a magnetic field;

means for sensing strength of said magnetic field: and means responsive to said sensing means for variable loading said magnetic field to regulate said magnetic field strength, said loading means loads said magnetic field to restrict said field to a predetermined maximum level.

7. A programmer according to claim 6, wherein said loading means loads said magnetic field to maintain a constant magnetic field.

8. A programmer according to claim 6, wherein said loading means comprises means for regulating Q of said transmitting antenna.

9. A programmer according to claim 6, wherein said sensing means comprises a sensing antenna reaching a predetermined level.

10. A programmer for transmitting information to an implantable medical device by means of a transmitter, said transmitter in turn comprising:

a transmitting antenna;

means for supplying a radio frequency signal to said transmitting antenna to cause generation of a magnetic field;

means for sensing strength of said magnetic field, said sensing means further comprises a sensing antenna; and means responsive to said sensing means for variably loading said magnetic field to regulate said magnetic field strength, said loading means comprises means for allowing current flow through said sensing antenna in response to said magnetic field reaching a predetermined level.

11. A transmitter system for use in a programmer useful to communicate with an implantable medical device comprising:

a transmitting antenna;

a power supply means connected via an amplifier to provide power to encoded signal for transmission by said transmitting antenna, secondary antenna means for receiving transmission by said transmitting antenna and for controlling Q of said transmitting antenna by absorbing transmitted power.

12. A transmitter system as set forth in claim 11 wherein said absorbed transmitted power is shunted to said power supply.

13. A transmitter as set forth in claim 11 wherein said absorbed transmitted power is supplied to said power supply means through connection thereto via a diode means.

\* \* \* \* \*